(12) United States Patent
Bercovici et al.

(10) Patent No.: US 10,527,584 B2
(45) Date of Patent: *Jan. 7, 2020

(54) CONTINUOUS CELL DETECTION BY ISOTACHOPHORESIS

(71) Applicant: TECHNION RESEARCH AND DEVELOPMENT FOUNDATION LIMITED, Haifa (IL)

(72) Inventors: Moran Bercovici, Haifa (IL); Ortal Schwartz, Haifa (IL)

(73) Assignee: Technion Research and Development Foundation Limited, Haifa (IL)

( * ) Notice: Subject to any disclaimer, the term of this patent is extended or adjusted under 35 U.S.C. 154(b) by 66 days.

This patent is subject to a terminal disclaimer.

(21) Appl. No.: 15/818,837

(22) Filed: Nov. 21, 2017

(65) Prior Publication Data
US 2018/0067077 A1    Mar. 8, 2018

Related U.S. Application Data

(63) Continuation of application No. 14/555,793, filed on Nov. 28, 2014, now Pat. No. 9,885,688.
(Continued)

(51) Int. Cl.
    *G01N 27/447*    (2006.01)
    *B01L 3/00*    (2006.01)

(52) U.S. Cl.
    CPC .... *G01N 27/44769* (2013.01); *B01L 3/50273* (2013.01); *G01N 27/44721* (2013.01);
    (Continued)

(58) Field of Classification Search
    CPC .......... G01N 27/447; G01N 27/44743; G01N 27/44769; G01N 27/44791;
    (Continued)

(56) References Cited

U.S. PATENT DOCUMENTS 6,107,038 A * 8/2000 Choudhary .......... B01J 19/0046
                                                      204/450
7,828,948 B1 * 11/2010 Hatch .................... B01D 57/02
                                                      204/455
(Continued)

OTHER PUBLICATIONS

Schwartz, Ortal et al., "Microfluidic Assay for Continuous Bacteria Detection Using Antimicrobial Peptides and Isotachophoresis", Analytical Chemistry, 2014, 86 (20), pp. 10106-10113.
(Continued)

*Primary Examiner* — Gurpreet Kaur
(74) *Attorney, Agent, or Firm* — Roach Brown McCarthy & Gruber, P.C.; Kevin D. McCarthy

(57) ABSTRACT

A system comprising a protein and a channel. The channel has a domain that binds a membranal component. The channel is configured to carry a liquid sample to an isotachophoresis (ITP) apparatus. The liquid sample comprising or suspected of comprising a cell, a cell membrane or a fraction of a cell membrane. The ITP apparatus comprises a first zone and a second zone. The first zone is configured to contain a solution of high effective mobility leading electrolyte (LE) ion. The second zone is configured to contain a solution of low effective mobility trailing electrolyte (TE) ion. The first zone and the second zone are configured to be operably connected to at least one anode and at least one cathode.

19 Claims, 6 Drawing Sheets

Specification includes a Sequence Listing.

Related U.S. Application Data

(60) Provisional application No. 61/910,131, filed on Nov. 29, 2013.

(52) U.S. Cl.
CPC . *G01N 27/44743* (2013.01); *G01N 27/44765* (2013.01); *G01N 27/44791* (2013.01); *B01L 2200/0652* (2013.01); *B01L 2300/06* (2013.01); *B01L 2300/0627* (2013.01); *B01L 2300/0887* (2013.01); *B01L 2300/12* (2013.01); *B01L 2400/043* (2013.01); *B01L 2400/0421* (2013.01)

(58) Field of Classification Search
CPC ....... G01N 27/44726; G01N 27/44756; G01N 27/44721; G01N 27/44765; G01N 33/56911; G01N 33/561; B01D 57/02; B01L 3/50273; B01L 2300/0887; B01L 2300/0645; B01L 2300/0816; B01L 2300/0867; B01L 2300/06
See application file for complete search history.

(56) References Cited

U.S. PATENT DOCUMENTS

| | | | |
|---|---|---|---|
| 9,753,007 B1* | 9/2017 | Chambers | B01D 57/02 |
| 2012/0061242 A1 | 3/2012 | Santiago | |
| 2012/0152746 A1 | 6/2012 | Santiago | |
| 2012/0160689 A1* | 6/2012 | Utz | C07K 1/26 |
| | | | 204/549 |
| 2014/0128313 A1* | 5/2014 | Bishop | C07K 7/06 |
| | | | 514/2.4 |

OTHER PUBLICATIONS

Oukacine, Farid et al., "Simultaneous Electrokinetic and Hydrodynamic Injection for High Sensitivity Bacteria Analysis in Capillary Electrophoresis", Analytical Chemistry, 2011, 83 (12), pp. 4949-4954.

Bahga, Supreet, S. et al, "High-sensitivity detection using isotachophoresis with variable cross-section geometry", Electrophoresis. Feb. 2011;32(5):563-72.

Phung, Sui Ching, "Rapid and sensitive microbial analysis by capillary isotachophoresis with continuous electrokinetic injection under field amplified conditions", Electrophoresis, Special Issue: Bioanalysis 2013, vol. 34, Issue 11, pp. 1657-1662, Jun. 2013.

Harrison et al. "Prediction of the location of stationary steady-state zone positions in counterflow isotachophoresis performed under constant voltage in a vortex-stabilized annular column" J Sep Sci. Dec. 2007 ; 30(18): 3255-3261 (15 pages).

Khurana et al., "Sample Zone Dynamics in Peak Mode Isotachophoresis" Anal. Chem. 2008, 80, 6300-6307 (8 pages).

Oukacine et al., "Study of Antibacterial Activity by Caplillary Electrophoresis Using Multiple UV Detection Points" Analytical Chemistry 2012, 84, 3301-3310.

\* cited by examiner

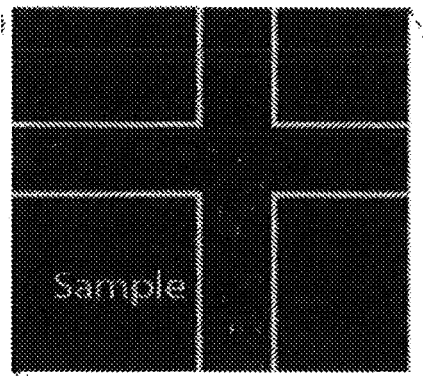
FIGURE 2B
FIGURE 2A
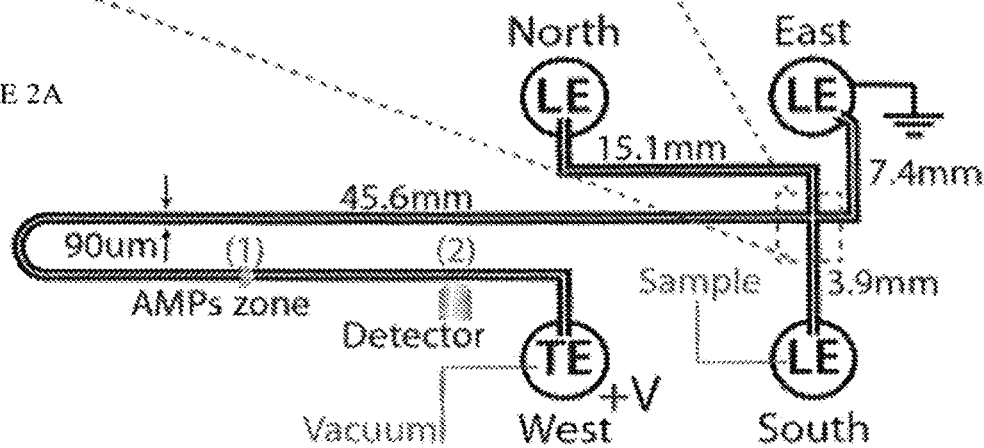
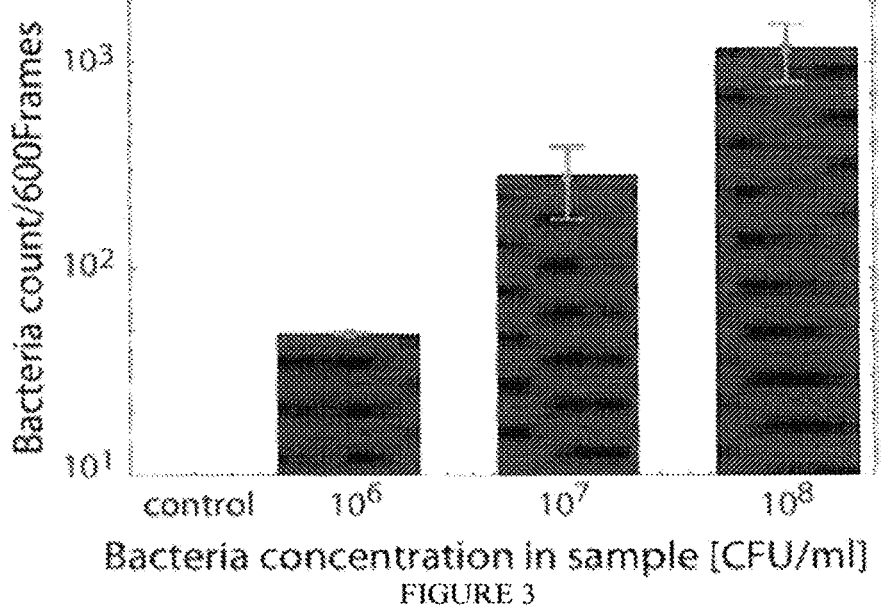
FIGURE 3

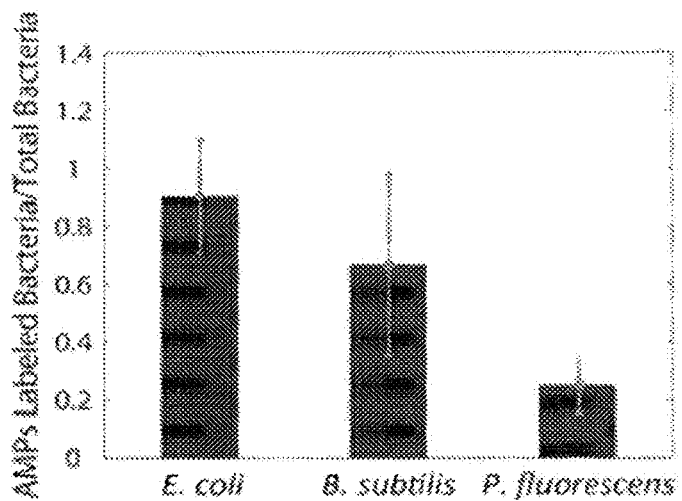
FIGURE 4C
FIGURE 5A
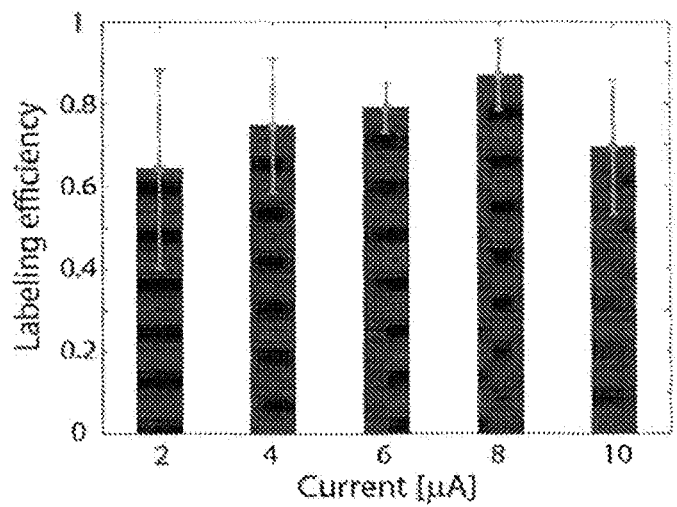
FIGURE 5B
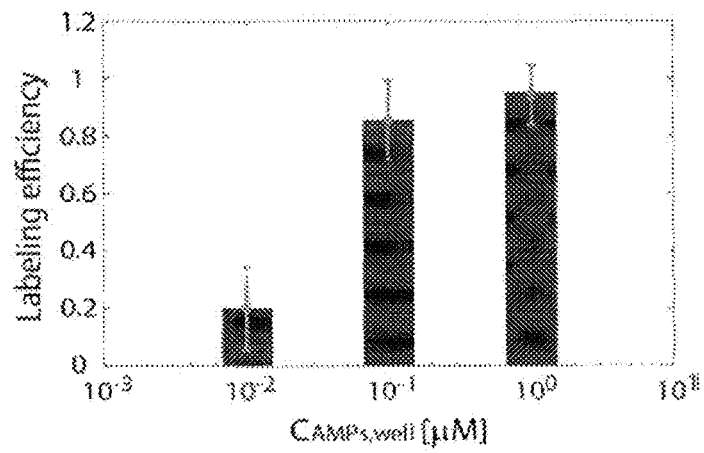

Original Image

Image with dilation

Image with filtering

FITC filter – SYTO9 prelabeled bacteria

TRITC filter – AMPS zone labeled bacteria

CONTINUOUS CELL DETECTION BY ISOTACHOPHORESIS

FIELD OF INVENTION

This invention is directed to; inter alia, an isotachophoresis system for the detection and/or separation of cells based on a membranal component detectable by a protein.

BACKGROUND OF THE INVENTION

Isotachophoresis

Isotachophoresis ("TTP") is a variant of electrophoresis, characterized by the fact that separation is carried out in a discontinuous buffer system. Sample material to be separated is inserted between a "leading electrolyte" and a "terminating electrolyte" or mixed in any of these, the characteristic of these two buffers being that the leader has to have ions of net mobility higher than those of sample ions, while the terminator must have ions of net mobilities lower than those of sample ions. In such a system, sample components sort themselves according to decreasing mobilities from leader to terminator, in a complex pattern governed by the so-called Kohlrausch regulating function. The process has been described repeatedly, as for instance, Bier and Allgyer, Electrokinetic Separation Methods 443-69 (Elsevier/North-Holland 1979).

It is further characteristic of ITP that a steady state is eventually reached, where all components migrate at same velocity (hence the name) in sharply defined contiguous zones. Sample components can be separated in such a contiguous train of components by insertion of "spacers" with mobilities intermediary between those of the components one wishes to separate.

Isoelectric focusing ("IEF"), also sometimes called electrofocusing, is a powerful variant of electrophoresis. The principle of IEF is based on the fact that proteins and peptides, as well as most biomaterials, are amphoteric in nature, i.e., are positively charge in acid media and negatively charged in basic media. At a particular pH value, called the isoelectric point (PI), there is reversal of net charge polarity, the biomaterials acquiring zero net charge.

If such amphoteric materials are exposed to a d.c. current of proper polarity in a medium exhibiting a pH gradient, they will migrate, i.e., 'focus' toward the pH region of their PI, where they become virtually immobilized. Thus a stationary steady state is generated, where all components of the mixture have focused to their respective PIs.

The pH gradient is mostly generated 'naturally' i.e, through the electric current itself. Appropriate buffer systems have been developed for this purpose, containing amphoteric components which themselves focus to their respective PI values, thereby buffering the pH of the medium.

The two variants, IEF and ITP, differ in that IEF attains a stationary steady state whereas in ITP a migrating steady state is obtained. Thus, in IEF a finite length of migrating channel is always sufficient. In ITP, complete resolution may require longer migrating channels than is practical. In such case, the migrating components can be virtually immobilized by applying a counterflow, the rate of counterflow being matched to the rate of frontal migration of the sample ions. This is also known in the art.

IEF is most frequently carried out in polyacrylamide or agarose gels, where all fluid flow disturbances are minimized. ITP is most often carried out in capillaries. The sample is inserted at one end of the capillary, at the interface between leader and terminator, and the migration of separated components recorded by appropriate sensors at the other end of the capillary. Both such systems are used mainly for analytical or micro-preparative purposes.

ITP forms a sharp moving boundary between ions of like charge. The technique can be performed with anionic or cationic samples. The system quickly establishes a strong gradient in electric field at the ITP interface, due to the non-uniform conductivity profile. As per its name (from Greek, "isos" means "equal", "takhos" means "speed"), TE and LE ions travel at the same, uniform velocity, as a result of the non-uniform electric field and conservation of current (this is the so-called "ITP condition").

The ITP interface is self-sharpening: LE ions that diffuse into the TE zone experience a strong restoring flux and return to the leading zone (and vice versa for TE ions in the LE zone). Sample ions focus at this interface if their effective mobility in the TE zone is greater than those of the TE co-ions, and if their effective mobility in the LE zone is less than that of the LE co-ions. The self-sharpening and focusing properties of ITP contribute to the robustness of this technique and make ITP relatively insensitive to disturbances of the interface (e.g. due to pressure-driven flow or changes in geometry, such as contractions, expansions, and turns).

In peak mode ITP, sample ion concentrations are at all times significantly lower than LE and TE ion concentrations and therefore contribute negligibly to local conductivity. The distribution of sample ions is determined by the self-sharpening interface between neighboring zones (here the TE and LE) and the value of the sample effective mobility relative to these zones. Multiple sample ions focus within the same narrow ITP interface region as largely overlapping peaks.

Pathogen Detection

The conventional bacteria detection methods—e.g. sample cultivation, genotypic detection methods and immunoassays—are time consuming, comprise of several manual steps, and require highly trained personnel. In recent years, there has been significant interest in the use of microfluidic platforms for pathogen detection. Microfluidic technology enables the manipulation and analysis of small volumes of sample, typically on the order of several nl to several µl and can be leveraged toward rapid and highly sensitive analysis.

Oukacine et al. (Anal. Chem. 2011, 83, 4949-4954) used simultaneous electrokinetic and hydrodynamic injection with UV detection and thus required no labeling. Prior to injection, sample was filtered and isolated from the original water matrix and then resuspended in a low conductivity electrolyte which was then used in the analysis. This method provided a limit of detection of $2 \times 10^4$ cfu/mL.

Another approach was explored by Phung et al. (Electrophoresis 2013, 34, 1657-1662) in order to improve the sensitivity of detection. Their assay involves a prelabeling step in which the sample was incubated with SYTO9 dye (a cell permeable nucleic acid stain) for approximately 30 min. This was followed by ITP focusing of bacteria from the sample and fluorescence detection of the formed peak. The assay was performed in a standard capillary electrophoresis apparatus and achieved a limit of detection of 135 cfu/mL. The authors have also demonstrated the detection of bacteria at a concentration of $\sim 10^4$ cfu/mL from contaminated river water samples, after filtering the sample to remove particulates.

However, despite the many advantages of this technology, to date, most microfluidic assays cannot perform continuous analysis and are limited by their ability to analyze only a single and finite amount of sample, and are thus coupled to significant sample preparation, e.g. by filtration or centrifugation. This is in contrast to the need for continuous and real time monitoring in many pathogen detection applications. Thus, there is an unmet need for rapid, continuous, effective, portable and more accurate detection and identification of infectious disease-causing pathogens, with the potential of automation and standardization.

SUMMARY OF THE INVENTION

In one embodiment, the present invention provides a system comprising:
(A) a protein having a domain that binds a membranal component;
(B) a first flow channel configured to provide flow of a liquid sample to an ITP system, said sample comprising or suspected of comprising a cell, a cell membrane or a fraction of a cell membrane; and
(C) an isotachophoresis (ITP) apparatus, said ITP apparatus comprises:
  (a) a first zone and a second zone, said first zone is configured to contain a solution of high effective mobility leading electrolyte (LE) ion, and said second zone is configured to contain a solution of low effective mobility trailing electrolyte (TE) ion, said first zone and said second zone are configured to be operably connected to at least one anode and at least one cathode; and
  (b) at least one second flow channel elongated between said first zone and second zone;
(D) a flow regulator, said flow regulator is configured to generate a flow countering an electromigration of said protein so as to maintain said protein in a pre-determined zone.

In another embodiment, the present invention provides a method for detecting or sampling a cell of interest, the method comprising the steps of: (a) providing a labeled protein having a domain that binds a membranal component, wherein said labeled protein is focused by ITP to an ITP zone in a liquid flow channel; (b) applying a counter flow so as to maintain said labeled protein in a stationary zone; (c) providing a sample to said flow channel, said sample comprising or suspected of comprising a cell of interest, a cell membrane or a fraction of a cell membrane thereof; and (d) detecting or sampling said cell of interest bound to said labeled protein.

BRIEF DESCRIPTION OF THE DRAWINGS

FIGS. 2A-B. A schematic illustration of an embodiment of the microfluidic chip layout and experiment setup. (2A) The chip is a commercially available design (NS-12A, PerkinElmer) made of isotropically etched soda lime glass with dimensions of 90 μm (width)×20 μm (depth). Also shown are the length dimensions of each intersected channel. A finite amount of AMPs is injected through the West reservoir, focused by cationic ITP, and remains confined and stationary at point (1) by negative pressure applied at the West reservoir. Electric field is applied on the channel by setting a constant voltage or current between East and West reservoirs, oriented for cationic ITP propagation from the West to the East. Detection of the fluorescent signal is obtained by a camera located at point (2), 4 mm downstream from the labeling zone. (2B) Raw fluorescence image of the channel intersection showing an *E. coli* sample prelabeled with SYTO9, initially mixed in the South reservoir, flowing into the main channel, toward the labeling site.

FIG. 3. Experimental results demonstrating quantitative bacterial detection, depicted in a bar graph providing detected bacteria flux (which is defined as the number of detected bacteria per frame) and correlated with the original bacterial concentration in sample. Thus, quantitative assessment of the original bacterial concentration was obtained. No signal was obtained for tap water used as the control case.

FIGS. 4A-C. 4A is a graph depicting experimental measurements of bacteria counts vs time, demonstrating continuous bacterial detection for 1 hour. The obtained signal exhibited stable behavior and increases linearly time. The signal was acquired by a CCD camera (iXon, Andor, Belfast Ireland) at The signal was acquired at a 1 Hz frame rate for 1 h. Constant voltage of 400 V was applied on the channel. Image analysis for bacteria detection was performed using MATLAB. 4B shows electric current trace of 1 hour operation of the assay. After an initial stage of formation of labeling zone, the height of the water column is manually controlled in order to maintain a stable electric current value (approximately 2 μA), indicating that the ITP interface is stationary. 4C is a bar graph showing a comparison of bacteria labeling efficiency for *Escherichia coli* ("*E. coli*"), *Bacillus subtilis* ("*B. subtilis*"), and *Pseudomonas fluorescens* ("*P. fluorescens*").

FIGS. 5A-B. Experimental results for characterization of labeling efficiency. (5A) Labeling efficiency as a function of applied current. Each measurement corresponds to analysis of pairs of FITC and TRITC images, acquired in 10 predetermined stations (total set of 20 images). Labeling efficiency was defined as the ratio between the number of detected bacteria in the TRITC images and the FITC images. For bacteria concentration in the sample, cB, equal to $10^8$ cfu/mL, the number of total detected bacteria in 10 stations ranged between 5 and 86 bacteria. The height of each bar represents the average of at least 3 realizations (5 repeats for 2.4 μA; 6 repeats for 6 μA; 3 repeats for 8 μA; 3 repeats for 10 μA), with the range of the bars representing 95% confidence of the mean. The mean labeling efficiency of the assay is ~75% regardless of the applied current value as was supported by t test statistical analysis which showed no significant difference (at 95% confidence) between the labeling efficiency at different electric current values. (5B) Dependence of bacteria labeling on AMPs concentration.

The results are shown as a function of the initial AMPs concentration in the reservoir. Constant current of 3 µA was applied on the channel. The height of each bar represents the average of 5 realizations for each concentration, with the range of the bars representing 95% confidence of the mean. Higher concentration results in better labeling, with no significant improvement beyond 0.1 µM as was demonstrated by t test statistical analysis.

Figure 6A:
Figure 6B:
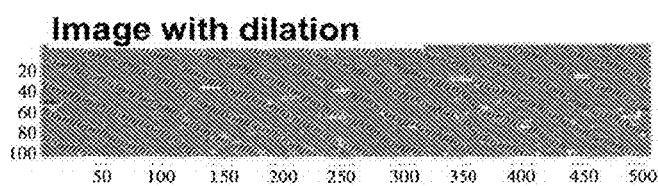
Figure 6C:
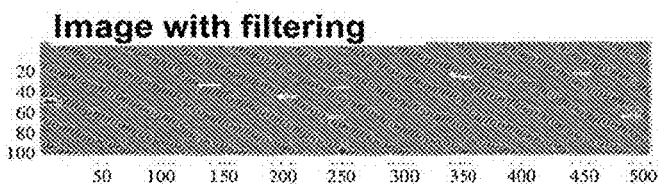

FIGS. 6A-C. Demonstration of the assay's image analysis process. (6A) A representative raw image acquired using a 200 ms exposure, 4 mm downstream from the ITP interface; (6B) The frame after background correction and dilation process; (6C) Final image with boundary traces, after size-based filtering, showing the detected bacteria in the frame.

Figure 7A:
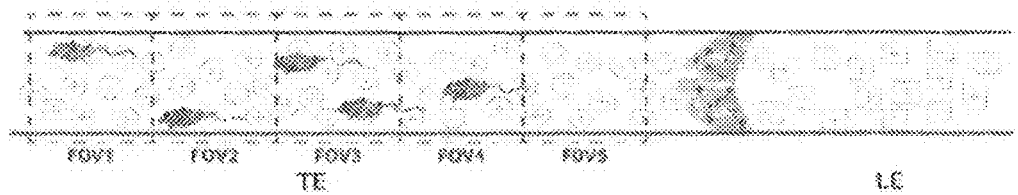
Figure 7B:
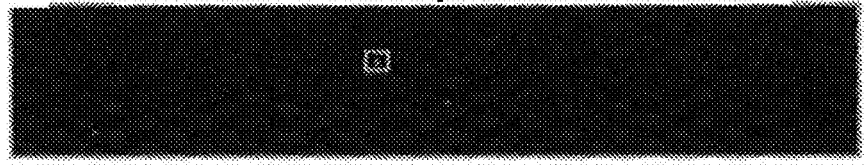

FIGS. 7A-B. Illustration of the image analysis procedure for measuring labeling efficiency. (7A) Downstream of the ITP interface zone, 10 adjacent fields of view (FOV) are defines along the detection zone. (7B) At each station, two images are acquired at two different wavelengths: using a 480/535 filter for detecting bacteria pre-labeled with SYTO9, and a 545/605 filter for detecting the bacteria labeled on-chip by AMPs. The bacterial detection algorithm is applied to the FITC image and for each detected bacteria, a search is performed for a corresponding signal in the TRITC image within an 8×8 pixel region around the center of the object.

Figure 8:
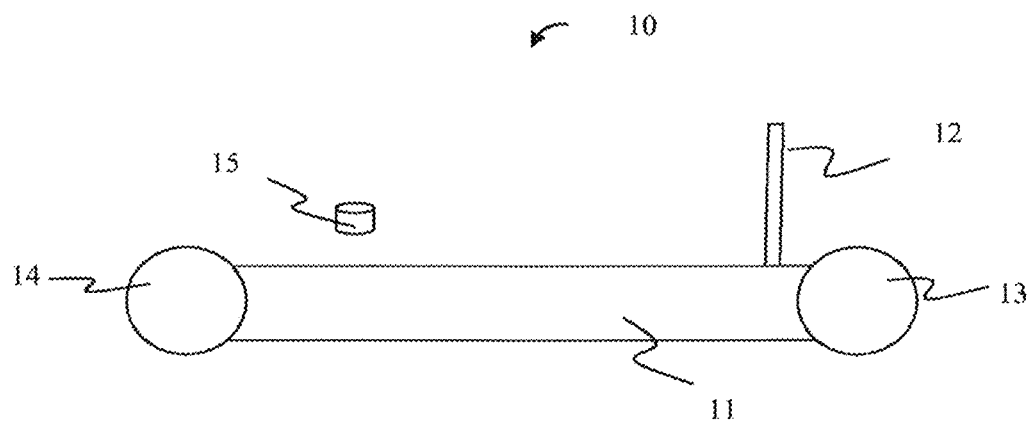

FIG. 8. A schematic illustration of an embodiment of the system of the invention.

DETAILED DESCRIPTION OF THE INVENTION

The present invention provides, in some embodiments, a micro fluidic system and assay for continuous, real-time, and quantitative detection of pathogens such as bacteria in water.

The present invention is based, in part, on leveraging ITP to focus peptide probes (e.g., antimicrobial peptides) in a confined region of a channel, through which cells (e.g., bacteria) can flow freely. This advantageously enables continuous labeling, separation, and detection of a cell (e.g., bacteria) or portions thereof, in a simple microchannel, without requiring any human intervention between steps. As exemplified herein below, the assay of the invention provided quantitative measurements with a stability of over 1 h of continuous monitoring using standard commercially available microfluidic chips.

Thus, in some embodiments the assay disclosed herein enables continuous monitoring of water at the point-of-need (e.g., water source, water treatment facilities, municipal networks, and even consumers), relieving the dependence on clinically trained personnel and eliminating the need to transport samples to a centralized lab. The use of a microfluidic platform, as well as the significant focusing of labeling probes by ITP, results in a significant reduction in the amount of expensive reagents required for detection and enables online continuous monitoring which is not possible in other applications. The assay may also be applicable for pathogen detection in food safety and medical diagnostics applications, where rapid pathogen detection is also crucial.

In one embodiment, the present invention provides a system comprising: (A) a protein having a domain that binds a membranal component; (B) a first flow channel configured to provide continuous flow of a liquid sample to an ITP system, said sample comprising or suspected of comprising a cell, a cell membrane or a fraction of a cell membrane; (C) an isotachophoresis (ITP) apparatus comprising a second flow channel; and a (D) a flow regulator, said flow regulator is configured to generate a flow countering an electromigration of said protein so as to maintain said protein in a pre-determined zone.

In another embodiment, said ITP apparatus comprises a first zone and a second zone, said first zone is configured to contain a solution of high effective mobility leading electrolyte (LE) ion, and said second zone is configured to contain a solution of low effective mobility trailing electrolyte (TE) ion, said first zone and said second zone are configured to be operably connected to at least one anode and at least one cathode; and at least one second flow channel elongated between said first zone and second zone.

In another embodiment, said ITP is an ITP system comprising: (1) a first zone comprising a solution of high effective mobility leading electrolyte (LE) ion; (2) a second zone comprising a solution of low effective mobility trailing electrolyte (TE) ion; (3) a flow generating means, wherein the flow generating means generates a flow countering an electromigration of the protein; and (4) an anode and a cathode.

In one embodiment, the present invention provides a system comprising: a protein having a domain that binds a membranal component; a cell, a cell membrane or a fraction of a cell membrane; a flow regulator or a flow generating means; and an isotachophoresis (ITP) system.

Reference is made to FIG. 8, which illustrates a system 10, constructed and operative in accordance with a non-limiting embodiment of the invention. System 10 includes a first zone 13 and a second zone 14, such as that said first zone is configured to contain a solution of high effective mobility leading electrolyte (LE) ion, and said second zone is configured to contain a solution of low effective mobility trailing electrolyte (TE) ion. For ITP assays, first zone 13 and second zone 14 are configured to be operably connected to at least one anode and at least one cathode. System 10 further includes a flow channel 11 (also denoted herein a second flow channel) elongated between said first zone and second zone. System 10 further includes a flow channel 12 (also denoted herein a first flow channel) providing an inlet for sample flow, such as continuous sample flow. In some embodiments, flow channel 12 is configured to provide continuous flow of a liquid or aqueous sample to flow channel 11 or first zone 13. System 10 may comprise one or more filters, such as along flow channel 12, said filters are configured to provide a sample free of waste which may alter or disturb the ITP focusing and/or binding of the cell or cell components. It is well within the skill of an ordinary art worker to determine the pore size of such a filter.

Further, system 10 included a flow regulator generate for generating a flow in channel 11, so as to counter an electromigration of a protein within the sample and maintain said protein in a pre-determined zone. In some embodiments, system 10 further includes a detector 15 as detailed hereinbelow.

In some embodiments, the sample is an environmental sample (e.g., water). In some embodiments, the sample is an industrial sample and/or food sample (e.g., liquid foods in raw or processed form, such as milk). Samples may be required to be prepared prior to analysis (e.g., extraction, dilution, filtration, centrifugation, and/or stabilization).

In another embodiment, said flow generating means is a flow regulator, said flow regulator is configured to generate a flow countering an electromigration of said protein so as to maintain said protein in a pre-determined zone. In another embodiment, the invention provides that the flow generating means generates flow countering an electromigration of the cell (bound or unbound to a protein as described herein). In another embodiment, the present invention further provides that the flow generating means is electroosmotic or pressure driven.

In another embodiment, a flow regulator or flow generating means is connected to the liquid tank of the ITP system or the aqueous solutions within the ITP. In another embodiment, a flow regulator or flow generating means is coupled to the liquid tank of the ITP system or the aqueous solutions within the ITP.

In some embodiments, said binding of a protein having a domain to a membranal component is a semi-selective binding. As used herein "semi-selective" binding refers to binding of the protein to multiple microbial species with differing affinities. In some embodiments, said binding of a protein having a domain to a membranal component is a selective binding.

In another embodiment, the membranal component is a net charge of phospholipid head groups. In another embodiment, the membranal component is a net charge of phospholipid head groups within a defined area of a membrane. In another embodiment, the membranal component is charge density of phospholipid head groups. In another embodiment, the membranal component is charge density of phospholipid head groups within a defined area of a membrane.

In another embodiment, the membranal component is a protein. In another embodiment, the membranal component is a membranal protein. In another embodiment, the membranal component comprises an immunoglobulin component. In another embodiment, the membranal component comprises a major histocompatibility complex (MHC) component. In another embodiment, the membranal component comprises a receptor. In another embodiment, the membranal component comprises a membrane receptor protein. In another embodiment, the membranal component comprises a transport protein. In another embodiment, the membranal component comprises a membrane enzyme. In another embodiment, the membranal component comprises a cell adhesion molecule. In another embodiment, the membranal component comprises an integral membrane protein. In another embodiment, the membranal component comprises an integral polytopic protein. In another embodiment, the membranal component comprises a beta barrel protein. In another embodiment, the membranal component comprises an integral monotopic protein. In another embodiment, the membranal component comprises a peripheral membrane protein. In another embodiment, the membranal component comprises a toxin. In another embodiment, the membranal component comprises a colicin. In another embodiment, the membranal component comprises a hemolysin. In another embodiment, the membranal component comprises an anti-microbial peptide (AMP) recognition site.

In another embodiment, the cell is an intact cell. In another embodiment, "cell" is a eukaryotic cell. In another embodiment, "cell" is a prokaryotic cell. In another embodiment, "cell" is a pathogenic cell. In another embodiment, "cell" is a solitary cell. In another embodiment, said cell is within an assembly of cells.

As used herein, the term "pathogen" refers to a microorganism which can cause disease in its host. Examples of pathogens suitable for detection in accordance with the present disclosure include bacteria, viruses, fungi, prions, and combinations thereof.

None limiting examples of cell that may be detected using the assay and method of the invention include: *Escherichia coli, Bacillus subtilis, Bacillus cereus, Bacillus thuringiensis, Bacillus coagulans, Bacillus anthracis, Francisella philomiragia, Vibrio cholera, Enterobacter aerogenes, Enterobacter cloacae, Klebsiella pneumoniae, Klebsiella oxytoca, Citrobacter koseri, Citrobacter freundii, Staphylococcus aureus, Staphylococcus epidermidis, Enterococcus faecalis, Enterococcus faecium, Streptococcus pneumoniae, Streptococcus pyogenes, Proteus mirabilis, Proteus vulgaris, Serratia marcescens, Morganella morganii, Pseudomonas aeruginosa, Pseudomonas syringae, Stenotrophomonas maltophilia, Acinetobacter baumannii, Acinetobacter lwoffii, Acinetobacter radioresistens, Acinetobacter johnsonii, Candida albicans, Candida parapsilosis* Enterobacteria phage MS2, Influenza A Virus, Influenza B Virus, *Cladosporium sphaerospermum, Sacchromyces cerevisiae,* and combinations thereof.

In another embodiment, a protein having a domain that binds a membranal component is an antibody. In another embodiment, a protein having a domain that specifically binds a membranal component is a SCFV. In another embodiment, a protein having a domain that specifically binds a membranal component is an anti-microbial peptide (AMP). In another embodiment, a protein having a domain that specifically binds a membranal component is an antibody fragment including single chain, light chain, heavy chain, CDR, E(ab")2, Fab, Fab', Fv, sFv, dsFv and dAb, or any combinations thereof. In another embodiment, a protein having a domain that specifically binds a membranal component is a membranal receptor ligand. In another embodiment, a protein having a domain that specifically binds a membranal component is a cell adhesion molecule binding protein. In another embodiment, a protein having a domain that specifically binds a membranal component is a cell adhesion protein. Determining and applying a protein having a domain that binds a membranal component to the methods and system described herein is within the skill of an ordinary art worker.

In another embodiment, a protein of the invention is a probe. In another embodiment, a protein of the invention is labeled. In another embodiment, a protein of the invention comprises a fluorescent label. In another embodiment, a protein of the invention comprises a radioactive label. In another embodiment, a protein of the invention comprises a chemiluminescent label. In another embodiment, a protein of the invention comprises a colorimetric label. In another embodiment, a protein of the invention serves as a probe and/or as an electrical charge quencher molecule for the identification and/or separation of a membranal component as described herein.

In another embodiment, the present invention further provides that the system as described herein comprises a photodetector, a photomultiplier tube (PMT), a conductivity detector, a radioactive detector, a camera or any combination thereof.

In another embodiment, the flow generating means is a pump. In another embodiment, the flow generating means is a reciprocating pump. In another embodiment, the flow generating means is a rotary pump. In another embodiment, the flow generating means is a mechanical pump. In another embodiment, the flow generating means is any pump known to one of skill in the art. In another embodiment, the flow generating means or pump generates a continuous flow. In another embodiment, the flow generating means or pump generates a uniform outflow. In another embodiment, the flow generating means or pump generates a uniform pressure. In another embodiment, the flow generating means or pump can be adjusted in terms of its pumping capacity, its outflow generation, its pressure generation or any combination thereof. In another embodiment, the flow generating means is adjusted to equally counter the flow of the protein of the invention. In another embodiment, the flow generating means is responsible for maintaining the stationary portion (non-migrating zone for the unbound protein) of the ITP wherein free protein is present. In another embodiment the sum of ITP electro-migration and counter-flow generated by the flow generating means with respect to unbound protein within the ITP system as described herein, is zero. In another embodiment, flow countering an electromigration is electroosmotic or pressure driven.

In another embodiment, the stationary zone is an anionic stationary zone characterized by high concentration of the protein. In another embodiment, the stationary zone is an anionic stationary zone characterized by high concentration of unbound protein. In another embodiment, the stationary zone is an anionic stationary zone free or substantially free of bound protein or protein complexes. In another embodiment, the stationary zone is an anionic stationary zone comprising all or most of the unbound protein with the ITP system.

In another embodiment, the stationary zone is a cationic stationary zone characterized by high concentration of the protein. In another embodiment, the stationary zone is a cationic stationary zone characterized by high concentration of unbound protein. In another embodiment, the stationary zone is a cationic stationary zone free or substantially free of bound protein or protein complexes. In another embodiment, the stationary zone is a cationic stationary zone comprising all or most of the unbound protein with the ITP system.

In another embodiment, the leading electrolyte (LE) buffer is chosen such that its ions (cations or anions) have higher effective electrophoretic mobility than the ions of the trailing electrolyte (TE) buffer. Effective mobility describes the observable drift velocity of an ion and takes into account the ionization state of the ion, as described in detail by Persat et al. In another embodiment, sample ions of intermediate effective mobility race ahead of TE ions but cannot overtake LE ions, and so they focus at the LE-TE interface (hereinafter called the "ITP interface"). In another embodiment, the LE and TE buffers are chosen such that have a higher mobility than the TE, but cannot overspeed the LE. In another embodiment, the TE and LE buffers form regions of respectively low and high conductivity, which establish a steep electric field gradient at the ITP interface. In another embodiment, the LE buffer (or LE) has a high ionic strength. In another embodiment, the LE buffer comprises Sodium hydroxide. In another embodiment, $Mg^{2+}$ ions are used as a counter ion to promote rapid hybridization. In another embodiment, TE buffer (or TE) comprises Pyridine. In another embodiment, LE comprises hydrochloric acid. In another embodiment, LE comprises 70 to 150 mM HCl and 150 to 280 mM Bistris (2,2-Bis(hydroxymethyl)-2,2',2"-nitrilotriethanol).

In another embodiment, LE comprises NaOH. In another embodiment, LE comprises 70 to 100mM NaOH. In another embodiment, LE comprises NaOH. In another embodiment, LE comprises 100 to 150 mM NaOH. In another embodiment, LE comprises NaOH. In another embodiment, LE comprises 120 to 150mM NaOH. In another embodiment, LE comprises 150 to 200 mM Hepes. In another embodiment, LE comprises 200 to 250 mM Hepes. In another embodiment, LE comprises 150 to 200 mM Bistris. In another embodiment, LE comprises 220 to 280 mM Hepes.

In another embodiment, ITP includes a microchannel connected to two reservoirs and is initially filled with LE solution. In another embodiment, a sample comprising a cell to be detected is mixed in the trailing electrolyte (TE) reservoir. In another embodiment, a sample comprising cell to be detected is mixed in the leading electrolyte (LE) reservoir. In another embodiment, an electric field induces the electromigration of all ions in the channel.

In another embodiment, a system as described herein further comprises a photodetector. In another embodiment, a system as described herein further comprises a photomultiplier tube (PMT). In another embodiment, a system as described herein further comprises a camera. In another embodiment, a system as described herein further comprises a radioactive probe or detector. In another embodiment, a system as described herein further comprises a calorimetric detector. In another embodiment, a system as described herein further comprises a conductivity detector.

In another embodiment, the present invention further provides a method for detecting a cell of interest, comprising the steps of: (a) Setting the ITP system of claim 1, wherein said protein is a labeled protein; (b) Applying an electric field across the first zone and the second zone; (c) Calibrating said flow generating means to create: (1) a stationary zone characterized by a high concentration of the labeled protein, and (2) a continuous flow of the cell of interest from the first zone to the second zone; (d) Adding a sample comprising the cell of interest through said flow generating means; and (e) Detecting the cell of interest bound to the labeled protein; Wherein both the cell of interest bound to the labeled protein and unbound cell of interest flow from the first zone to the second zone while unbound labeled protein remains within the stationary zone, thereby detecting a cell of interest.

In another embodiment, the present invention provides a method for detecting a cell of interest, the method comprising the steps of: (a) providing a labeled protein having a domain that binds a membranal component, wherein said labeled protein is focused by ITP to an ITP zone in a liquid flow channel; (b) applying a counter flow so as to maintain said labeled protein in a stationary zone; (c) providing a sample to said flow channel, said sample comprising or suspected of comprising a cell of interest, a cell membrane or a fraction of a cell membrane thereof; and (d) detecting said cell of interest bound to said labeled protein.

In another embodiment, the present invention provides a method for detecting and/or sorting cells. In another embodiment, the present invention provides a method for detecting and/or sorting cells wherein cells are continuously introduces into one of the aqueous solutions (TE or LE). In another embodiment, the present invention provides a method for detecting and/or sorting cells wherein cells are continuously infused into one of the aqueous solutions (TE or LE). In another embodiment, the present invention provides that the cells are continuously infused via the flow generating means. In another embodiment, the present invention provides that the cells are continuously infused via an infusing means.

In another embodiment, the term "detecting" includes labeling, separating, enriching, identifying, sorting, isolating, or any combination thereof. In another embodiment, detecting is quantitative, qualitative, or both. In another embodiment, detecting is achieved by using a photodetector, a sensor, an affinity column, a photomultiplier tube (PMT), a conductivity detector, a radioactive detector, a light detector, an emission detector, a camera or any combination thereof.

In another embodiment, the present invention provides an ITP kit comprising the system as described herein and specific instructions for performing the method as described herein. In another embodiment, the present invention provides a kit comprising an instruction manual describing the method and/or system disclosed herein. In another embodiment, the present invention provides a kit as described herein further comprising an electrophoresis apparatus. In another embodiment, the present invention provides a kit as described herein further comprising an electrophoresis apparatus that is communicatively coupled to a central processing unit (including but not limited to a central processing unit (CPU), ASIC or FPGA, that may operate the electrophoresis apparatus based on a predetermined set of instructions.

In another embodiment, detecting is detecting a specific cell type or a fragment thereof. In another embodiment, detecting is detecting cell marker on the cell's membrane. None limiting examples of pathogens that can be detected in water samples using the methods described herein include protozoa such as those of the genus *Cryptosporidium* and the genus *Giardia*; bacteria such as *Escherichia coli, Yersinia pestis, Francisella tularensis, Brucella species, Clostridium perfringens, Burkholderia mallei, Burkholderia pseudomallei, Chlamydia psittaci, Coxiella burnetii, Rickettsia prowazekii, Vibrio species; Enterococcus faecalis; Staphylococcus epidermidis; Staphylococcus aureus; Enterobacter aerogenes; Corynebacterium diphtheriae; Pseudomonas aeruginosa; Acinetobacter calcoaceticus; Klebsiella pneumoniae; Serratia*; yeasts such as *Candida albicans*; and viruses, including filoviruses such as Ebola and Marburg viruses, naviruses such as Lassa fever and Machupo viruses, alphaviruses such as Venezuelan equine encephalitis, eastern equine encephalitis, and western equine encephalitis, rotoviruses, calciviruses such as Norwalk virus, and hepatitis (A, B, and C) viruses, and biological warfare agents such as smallpox (i.e., variola major virus).

In another embodiment, the system of the invention is set including introducing the protein that may serve as a probe into the TE or LE solution, applying electrical field between the LE and the TE zones and a counterflow at the same time while adjusting the electrical field and the counterflow to values that permit the formation of a stationary zone-wherein the protein is captured, actuating the detection means, and adding a cell or a cell fragment, wherein cells or cell fragments labeled by the protein but not unbound protein-migrate and wherein a detector set at a location after the stationary zone in the direction of electromigration is configured to detect protein labeled membranes but not cells free of the protein probe. In another embodiment, a detector set at a location after the stationary zone in the direction of electromigration is configured to detect and differentiate between both protein labeled membranes and cells free of the protein probe. In another embodiment, a detector set at a location after the stationary zone in the direction of the flow is configured to separate between protein labeled membranes and cells free of the protein probe.

In another embodiment, a method, a system and a kit as described herein may include a separation and/or isolation in one device or two separate devices. In another embodiment, the second step includes subjecting the migrating protein labeled cells to an electric field thus further isolating these probed cells according to their isoelectric point. In another embodiment, the separating means is a column which is capable of separating/distinguishing "naked" cells from protein probed cells.

In another embodiment, the present invention provides methods, systems and kits that reduce false positive or false negative results. In another embodiment, the present invention provides methods, systems and kits that reduce background noise. In another embodiment, the present invention provides methods, systems and kits that provide accurate quantitative measurements of cells of interest. In another embodiment, the present invention provides methods, systems and kits that provide an efficient separating technique for a cell of interest. In another embodiment, the present invention provides methods wherein the free, unhhybridized, protein is focused in a stationary zone.

In another embodiment, the protein is labeled. In another embodiment, the label is Acridine orange. In another embodiment, the label is Acridine yellow. In another embodiment, the label is Alexa Fluor. In another embodiment, the label is 7-Aminoactinomycin D. In another embodiment, the label is 8-Anilinonaphthalene-1-sulfonic acid. In another embodiment, the label is an ATTO dye. In another embodiment, the label is Auramine-rhodamine stain. In another embodiment, the label is Benzanthrone. In another embodiment, the label is Bimane. In another embodiment, the label is 9,10-Bis(phenylethynyl)anthracene. In another embodiment, the label is 5,12-Bis(phenylethynyl)naphthacene. In another embodiment, the label is Bisbenzimide. In another embodiment, the label is a Blacklight paint. In another embodiment, the label is Brainbow. In another embodiment, the label is Calcein. In another embodiment, the label is Carboxyfluorescein. In another embodiment, the label is Carboxyfluorescein diacetate succinimidyl ester. In another embodiment, the label is Carboxyfluorescein succinimidyl ester. In another embodiment, the label is 1-Chloro-9,10-bis(phenylethynyl)anthracene. In another embodiment, the label is 2-Chloro-9,10-bis(phenylethynyl)anthracene. In another embodiment, the label is 2-Chloro-9,10-diphenylanthracene. In another embodiment, the label is Coumarin. In another embodiment, the label is DAPI. In another embodiment, the label is a Dark quencher. In another embodiment, the label is DiOC6. In another embodiment, the label is DyLight Fluor. In another embodiment, the label is Ethidium bromide. In another embodiment, the label is Fluo-3. In another embodiment, the label is Fluo-4. In another embodiment, the label is a FluoProbe. In another embodiment, the label is Fluorescein. In another embodiment, the label is Fluorescein isothiocyanate. In another embodiment, the label is a Fluoro-Jade stain. In another embodiment, the label is Fura-2. In another embodiment, the label is Fura-2-acetoxymethyl ester. In another embodiment, the label is GelGreen. In another embodiment, the label is GelRed. In another embodiment, the label is Green fluorescent protein. In another embodiment, the label is a Heptamethine dye. In another embodiment, the label is Hoechst stain. In another embodiment, the label is Indian yellow. In another embodiment, the label is Indo-1. In another embodiment, the label is Lucifer yellow. In another embodiment, the label is Luciferin. In another embodiment, the label is MCherry. In another embodiment, the label is Merocyanine. In another embodiment, the label is Nile blue. In another embodiment, the label is Nile red. In another embodiment, the label is an Optical brightener. In another embodiment, the label is Perylene. In another embodiment, the label is Phloxine. In another embodiment, the label is P cont. In another embodiment, the label is Phycobilin. In another embodiment, the label is Phycoerythrin. In another embodiment, the label is Phycoerythrobilin. In another embodiment, the label is Propidium iodide. In another embodiment, the label is Pyranine. In another embodiment, the label is a Rhodamine. In another embodiment, the label is RiboGreen. In another embodiment, the label is RoGFP. In another embodiment, the label is Rubrene. In another embodiment, the label is (E)-Stilbene. In another embodiment, the label is (Z)-Stilbene. In another embodiment, the label is a Sulforhodamine. In another embodiment, the label is SYBR Green I. In another embodiment, the label is Synapto-pHluorin. In another embodiment, the label is Tetraphenyl butadiene. In another embodiment, the label is Tetrasodium tris(bathophenanthroline disulfonate)ruthenium(II). In another embodiment, the label is Texas Red. In another embodiment, the label is Titan yellow. In another embodiment, the label is TSQ. In another embodiment, the label is Umbelliferone. In another embodiment, the label is Yellow fluorescent protein. In another embodiment, the label is YOYO-1. In another embodiment, the label is a chemiluminescent dye. In another embodiment, the label is a radioisotope or a radioactive dye. In another embodiment, the label is a dye that can be detected by a naked eye.

In another embodiment, the protein is a peptide. In another embodiment, the protein is a polypeptide. In another embodiment, the protein is a glycoprotein.

In another embodiment, the invention provides that cells migrate wherein unbound protein remains within the stationary zone. In another embodiment, the invention provides that protein probed cells migrate slower compared to unprobed cells.

In another embodiment, the method of the present invention can be utilized to identify pathogens. In another embodiment, the method of the present invention can be utilized to identify certain bacteria. In another embodiment, the method of the present invention can be utilized to identify any bacteria. In another embodiment, the method of the present invention can be utilized to identify a desired cell type such as but limited to a transfected cell, an immune cell, a cancer cell, a blood cell, a muscle cell, or any other known cell type carrying an identifiable mark on its membrane.

In another embodiment, the present method requires minimal or no sample preparation. In another embodiment, the theory behind ITP is provided in Bahga S S, Kaigala G V, Bercovici M, Santiago J G. High-sensitivity detection using isotachophoresis with variable cross-section geometry. Electrophoresis. 2011 February; 32(5):563-72; Khurana T K, Santiago J G. Sample zone dynamics in peak mode isotachophoresis. Anal Chem. 2008 Aug. 15; 80(16): 6300-7; and Isotachophoresis: Theory, Instrumentation and Applications. F. M. Everacrts, J. L. Beckers, T.P.E.M. Verheggen, Elsevier, Sep. 22, 2011, which are hereby incorporated by reference in their entirety.

In another embodiment, ITP is performed in a peak mode. In another embodiment, ITP is performed in a plateau mode. In another embodiment, "Plateau mode" refers to a wide sample-zone compared to the transition zones, i.e. the sample concentration distribution forms a plateau with blurred boundaries towards LE and TE. In another embodiment, "Peak mode" refers to a very short sample zone, where the two transition zones at both sides of the sample overlap or when the sample is entirely within the interface between LE and TE.

The sensitivity of the assay described herein is governed by the incoming flow rate of the sample. Thus, in some embodiments, larger channel dimensions can be used for achieving improved sensitivity. The microfluidic channel exemplified herein is a standard commercially available design (90 µm wide and 20 µm deep) and provided a LOD of approximately $10^4$ cfu/mL over a 60 min detection window. A set of 100 such parallel channels would have a total width of only 1 cm and would enable a LOD of approximately $10^2$ cfu/mL over a 1 h window.

In additional embodiments, increased flow rate can be achieved by maximizing the applied electric field on the channel, thereby increasing flow velocity. The labeling efficiency experiments demonstrated hereinbelow revealed that at least a 10-fold increase in the applied current is possible without affecting the labeling efficiency and impairing detection. Hence, designing a dedicated microfluidic chip, using the same principles presented here, may allow one to detect a concentration as low as $10^2$ cfu/mL in minutes.

In additional embodiments, higher throughput could also be achieved by using a larger diameter channel or capillary, but as temperature due to joule heat scales with the diameter, this would lead to excessive heating and require specialized cooling. In contrast, the use of multiple parallel channels in a planar format maintains the depth of the channel, and thus, temperature is expected to remain essentially unchanged. Higher throughput and longer analysis time would also require scaling the size of the reservoirs to avoid pH changes due to hydrolysis. As detailed by Persat et al. (Chips & Tips (Lab on a Chip), 2007; 1-8), operating the assay at 200 µA with a 100 mM LE, without exceeding a pH change of 0.2 in the reservoirs, would require a reservoir volume of 1.2 mL for 10 h of operation. This is a sufficiently small volume to be easily integrated with a microfluidic system.

Reference is made to Examples 1-2, demonstrating the assay of the invention using AMPs, which are relevant for detecting bacteria but do not provide information on the bacterial strain or species. Nonspecific detection of bacteria is useful in water monitoring as an early alert step and a first warning sign but still cannot be compared to the advantages of specific detection. In some embodiments, specific antibodies may be used as probes for particular pathogen strains. As many bacteria species are negatively charged over a wide range of pH (Harden and Harris, Bacteriol. 1953, 65, 198), it may be necessary to apply conditions in which the antibodies are positively charged and remain active, and their effective mobility is bracketed between those of the leading and trailing electrolytes. Most antibodies produced in mammals have pI values between 6.1 and 8.5 (Amersham Pharmacia Biotech Antibody Purification: Handbook; Amersham Pharmacia Biotech: Piscataway, N.J., 2000). Thus, by designing a cationic ITP buffer system at a pH <6, it may be possible to focus the majority of antibodies and apply the assay disclosed herein for detection of specific bacteria strains or species.

The method demonstrated here also has an inherent capability to operate with the use of only very small volumes of reagents due to the ITP focusing. The typical reagent amounts used in other AMP-based methods for bacteria detection ranges between 450 and 2500 ng. In contrast, the assay disclosed herein may use only 4.6 ng of AMPs in the reservoir. This amount can be even further reduced by allowing more focusing of the AMPs at the ITP interface during the formation of the labeling zone.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Chemicals and AMPs.

ITP Buffers. Cationic ITP was performed using LE buffer composed of 100 mM NaOH and 200 mM HEPES and TE buffer composed of 10 mM pyridine and 20 mM HEPES. To suppress electroosmotic flow (EOF), ~1% 1 MDa poly (vinylpyrrolidone) (PVP) was added to both buffers. All buffer components were purchased from Sigma-Aldrich, (St. Louis, Mo.) and prepared in purified UltraPure DNase/RNase free distilled water (Milli-Q water purification, Millipore Corp., Billerica, Mass., USA).

AMPs. TAMRA labeled Indolicidin, 5-TAMRA-ILPWK-WPWWPWRR (SEQ ID NO: [1]), synthesized by Biomatik (Wilmington, Del., USA) was used in the current study. Indolicidin is present in nature in bovine neutrophils and demonstrates broad spectrum of activity against Gram-negative and Gram-positive bacteria, fungi, and protozoa. A stock solution was prepared by solubilizing the AMPs in 1 to 8 acetonitrile in deionized water and stored at −20° C. Further dilutions were freshly prepared in acetonitrile before each set of experiments from a stock solution concentration of 100 µM which was kept refrigerated.

The peptide properties were estimated using the Pep-Calc.com online calculator. The pI of the peptide is at pH 12.41, and at a neutral pH, the overall charge is +2. Thus, it can likely be considered as a fully ionized cationic species in all experiments.

The AMPs mobility was estimated to be around $5 \times 10^{-9}$ m$^2$/(Vs) by observing the focusing of sample in a set of ITP experiments with various TE compositions having different effective mobilities. A tendency of the AMPs to attract and adhere to the negatively charged channel walls was noticed, likely due to electrostatic interaction. Thus, stringent cleaning of the channels between experiments was necessary. In addition, at very high concentrations (above 10 µM), aggregation and precipitation of AMPs was noticed, which can result in precipitants flowing toward the detector causing false positives. To avoid this, smaller concentrations of AMPs were used (as indicated hereinbelow) and introduced to the channel only a finite amount of AMPs which remains at a soluble concentration when focused.

Bacteria Growth Conditions and Sample Preparation.

Bacteria Growth Conditions. E. coli O:416 was used as a model strain in this study. Stock cultures were prepared by incubating E. coli in Luria broth (LB) at 37° C. to an OD600 of 0.3, corresponding to approximately $3 \times 10^8$ cfu/mL, as measured by standard plating. Thereafter, 1 mL of cell suspensions was transferred to sterilized 1.5 mL vials, centrifuged at 14650 rpm for 2 min, and discarded the supernatant. The centrifugation process was repeated twice to remove any medium remnants and stored the bacteria pellets at −20° C.

Sample Preparation. For experiments performed with unlabeled bacteria, pellets were resuspended in 1 mL of tap water and serially diluted in tap water to the final concentrations. For labeling efficiency experiments performed with prelabeled bacteria, the pellets were incubated in 200 µL of tap water and 4 µL of 34 µM SYTO9 BacLight (LIVE/DEAD BacLight Bacterial Viability Kit, Life technologies) for 10 min. To discard remaining free fluorophores, the pellet was centrifuged at 14650 rpm for 2 min, then removed supernatant, and resuspended the pellets in 1 mL of tap water, for a final concentration of $3 \times 10^8$ cfu/mL.

Experimental and Imaging Settings.

All experiments were performed on a NS-12A microchip made of isotropically etched soda lime glass (PerkinElmer, Waltham, Mass., USA). An overview of the chip geometry is provided in FIG. 2. The chip consists of two intersecting channels, each having maximum width and depth of 90 and 20 µm, respectively. Images were obtained using an inverted epifluorescent microscope (Ti-U, Nikon, Tokyo, Japan) equipped with a metal halide light source (Intensilight, Nikon Japan), 20× objective (Plan Fluor, NA=0.75, WD=0.66 mm, Nikon, Tokyo, Japan), TAMRA compatible filter-cube (model 49004, 545/25 nm excitation, 605/70 nm emission, and 565 nm dichroic mirror, Chroma, Bellows Falls, Vt., USA), SYTO9 compatible filter-cube (480/15 nm excitation, 535/20 nm emission, and 505 nm dichroic mirror, Nikon, Tokyo, Japan), and motorized stage (MS-2000, Applied Scientific Instrumentation, Eugene, Oreg.). Images were captured using a 14 bit, 512×512 pixels CCD camera (Clara, Andor, Belfast, Ireland). The camera and stage were controlled using NIS Elements software (v.4.11, Nikon, Tokyo, Japan) and processed the images with MATLAB (R2011b, Mathworks, Natick, Mass.). Constant voltage or current were applied using a sourcemeter (model 2410, Keithley Instruments, Cleveland, Ohio).

Assay Procedure.

Before each experiment, the channel was cleaned by sequentially flowing bleach and DI water, for 2 min each. In each experiment, first, a stationary ITP zone containing focused AMPs was established and then the sample was introduced into the channel.

Initial Formation of Labeling Zone. For chip loading, the North, East, and South reservoirs were filled with 20 µL of LE and applied vacuum at the West reservoir for 1 min to fill the channel. Next, the West reservoir was rinsed with DI water and filled it with 18 µL of TE and 2 µL of 1 µM AMPs. Constant voltage was applied between the West and East reservoirs. When the focused AMPs plug traveled a distance of 6 mm along the channel, the voltage was stopped, the West reservoir was rinsed, and 20 µL of pure TE was filled in it. Thereafter, the voltage (or current) was reapplied to regain focusing of the injected AMPs. This resulted in a finite and well controlled amount of focused AMPs. To then hold the AMPs plug stationary, negative pressure was applied to the West reservoir using a water column, resulting in pressure driven flow countering electromigration. The flow rate was controlled by changing the height of the water column according to visual monitoring of the ITP interface progression and feedback on the current reading, which is a good indication for the location of the interface in the channel. The AMPs plug, i.e., the labeling reaction zone, was positioned stationary 12 mm from the West reservoir (marked as station (1) in FIG. 2).

Detection Procedure. 10 μL of the sample of interest was introduced to the South reservoir followed by actuation of the pipet several times to homogenize the solution. For time dependent detection, the objective was positioned 4 mm downstream from the labeling reaction zone (marked as station (2) in FIG. 2) and the camera was triggered at 5 Hz for 2 min. For labeling efficiency experiments, the same procedure was used, but the spiked samples were also prelabeled with SYTO9 (labeling procedure described above). After turning off the electric field (and counter flow), images were captured at 10 stations downstream from the interface zone using both FITC and TRITC filters (total set of 20 images).

Bacteria count. In the continuous mode of the assay, the signal corresponds to a bacterial count in each recorded frame (ultimately providing the bacterial flux). As illustrated in FIG. 6, each raw image is analyzed using the following procedure implemented in Matlab: Since bacteria are sparse elements in each frame, the average intensity value of the frame is treated as an approximation for the background noise. The background is subtracted from the entire image. Further, a horizontal 4 pixels length line structuring element is constructed, which is used to dilate the background subtracted image. Boundary and edge trace functions are then used to find the boundaries of all elements in the dilated image and are finally, discarded by size and angle conditions the "noise" elements, and remaining closed regions are counted as bacteria.

Labeling efficiency. As illustrated in FIGS. 7A-B, pairs of FITC and TRITC images, acquired at 10 predetermined stations, are analyzed. The same bacteria count procedure as described herein was used to trace separately the bacteria in the FITC and TRITC images. For each bacteria found in the FITC image (corresponding to the SYTO9 channel), a region of 8×8 pixels in the corresponding TRITC image was searched for an overlapping signal. The labeling efficiency was calculated as the ration between the total number of elements detected in the TRITC images and the number of element detected in the FITC image.

Current monitoring. A constant voltage of 400V was applied on the channel. Initially, there is a decrease in current which indicates the formation of a propagating ITP front in the channel. At approximately 40 sec, the voltage is switched off as part of the AMPs injection process (TE reservoir is cleaned and replaced with pure TE), and then reestablished to regain focusing. Negative pressure is applied by changing the height of the water column connected to the TE reservoir. This results in pressure driven flow that opposes the ITP interface migration, and maintains in stationary. As the interface stabilizes in place, so does the electric current value. Tracking the current change in real time, the high tog the water column is manually adjusted to keep the current stable and thus hold the ITP zone at the same location.

Example 1

Microfluidic Assay for Continuous Real-Time Pathogen Detection Using Antimicrobial Peptides and Isotachophoresis The basic assumption for the following experiment was that PNAs targeting bacteria by non-specific binding to their negatively charged outer-membrane can be used as the protein as described herein and the bacteria to be detected can be the cell to be detected as described herein.

Figures 1A, 1B:
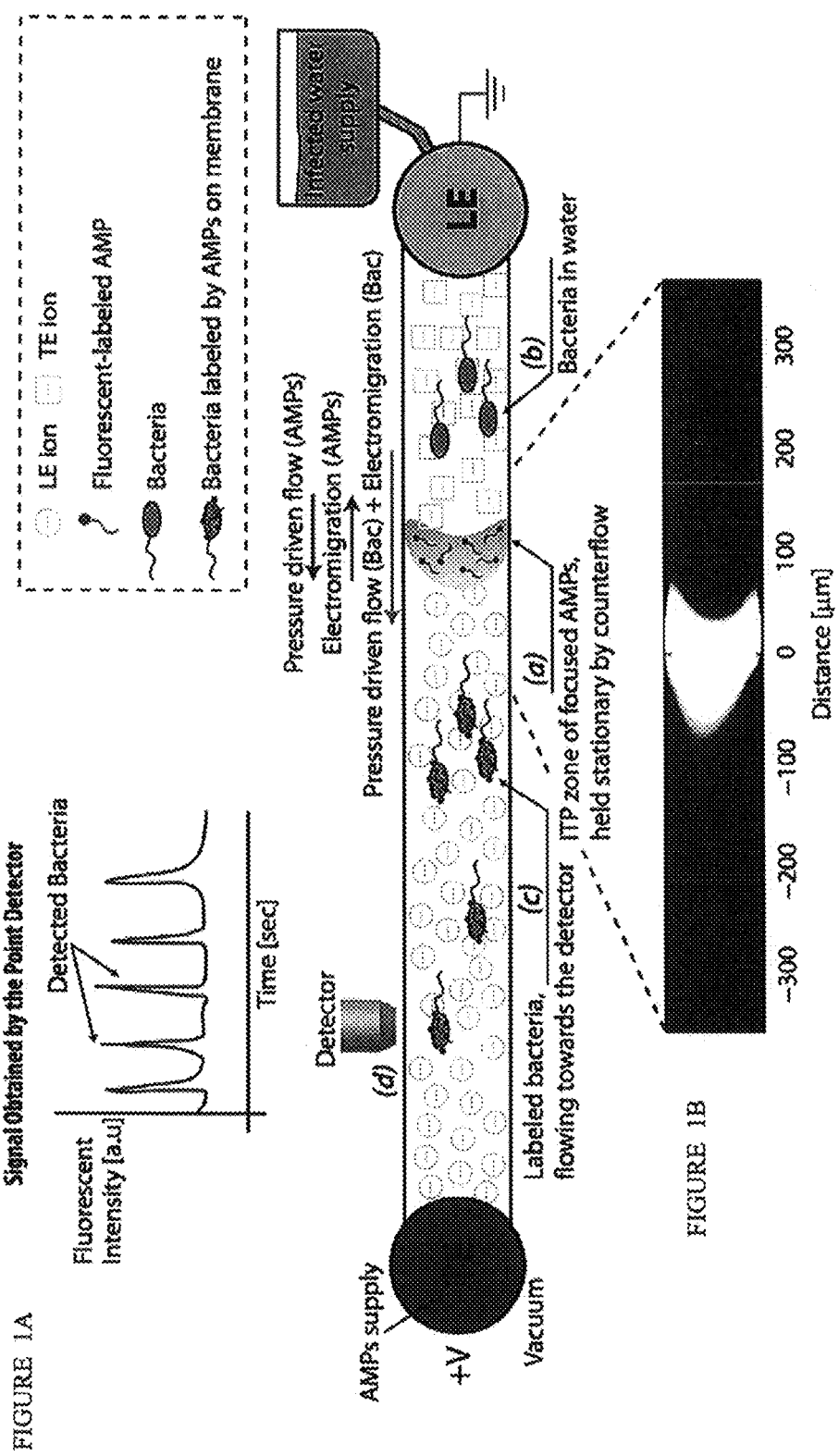
FIGS. 1A-B. (1A) A schematic illustration of an embodiment of the assay. (a) Fluorescently labeled AMPs, initially mixed in the trailing electrolyte (TE) reservoir, are focused by cationic ITP and held stationary using vacuum-driven counterflow applied at the TE reservoir. (b) The same vacuum line also continuously draws a flow of potentially infected sample from the leading electrolyte (LE) reservoir. (c) Any bacteria present in the sample travels through the high concentration AMPs zone, and is instantaneously labeled due to the locally accelerated reaction. The labeled bacteria continue downstream, while free AMPs remain confined to the stationary ITP zone, thus reducing the downstream background signal. (d) Further downstream the fluorescent signal is registered by a detector. The peaks in the signal, which correspond to individual bacteria passing through the detector, are counted and yield the bacteria concentration in sample. (1B) Fluorescent microscopy image demonstrating the labeling of E Coli O:416 with AMPs in the high concentration zone. A finite sample of AMPs is focused by ITP and held in place by pressure driven flow opposing the ITP progress. Initially unlabeled bacteria that flow through the zone are instantaneously labeled and can be clearly seen emerging for the interface. Free AMPs remain contained in the ITP zone.

An ITP system such as illustrated in FIG. 1 was used for the current experiments. The system included the settings as described herein. Specifically, positively charged labeled AMPs are universal probes for labeling and detecting bacteria. Using cationic ITP focusing, a high concentration zone of AMPs within a microchannel was formed. A pressure driven flow countering electromigration was applied to hold the zone stationary. Through this "virtual reaction chamber" the sample of interest was flowing (from the LE reservoir). Any bacteria present in the sample was simultaneously labeled by the AMP, and separated from, the high concentration AMPs, and continued downstream to a detector. This enabled continuous, real-time, quantitative one step labeling and detection of bacteria in sample. This experiment included ITP with fluorescently-labeled anti-microbial peptides (AMPs).

FIGS. 3 and 4 demonstrate the ability of the method to achieve continuous and quantitative bacteria detection in water samples. FIG. 3 presents the measured bacteria flux versus the known bacteria concentration introduced in the reservoir. Here, the bacteria in the sample are originally unlabeled and obtain their fluorescent labeling as they pass through the high concentration AMPs region. Images are recorded at a distance of 4 mm downstream from the ITP interface, and the number of bacteria in each frame is counted, as described hereinbelow. After binding to the outermembrane of the target bacteria, the AMPs may lyse and disrupt it as part of their killing mechanism. However, as this process typically takes several minutes and the detection of the assay described herein takes place only a few seconds after the binding, significant effect on the detection is not expected.

The acquired signal (i.e., bacterial flux) is proportional to the original bacterial concentration in the sample, illustrating that quantitative detection of *E. coli* can be obtained. Two sample t test method were used to determine whether the difference between any two measured mean values is significant. A p-value of p=0.05 (corresponding to 95% confidence on a statistical difference between results) was defined. In all cases, the calculated t-values were significantly higher than the required threshold (for example, the calculated t-value for the difference between the signal at $10^6$ and $10^7$ cfu/mL is 5.26, whereas the threshold based on the number of repeats is 2.57), indicating clear statistical significance. The limit of detection is determined by the flow rate of sample into the channel. Here, for channel cross section of 90 μm×20 μm, ITP velocity of $u_{ITP}$=100 μm/s, and approximated bacteria mobility of $\mu_B$=-30×10$^{-9}$ m$^2$/(V s), the bacterial flux for the $10^8$ cfu/mL sample is 1542 cfu/min. This is in good agreement with the order of magnitude of measured experimental values. Under these conditions, the lowest concentration detected in 2 min was $10^6$ cfu/mL; in this time period, approximately 40 bacteria pass through the ITP interface, get sufficiency labeled, and are detected. The extrapolated limit of detection is thus $10^5$ cfu/mL (yielding 4 bacteria in 2 min).

Figure 4A:
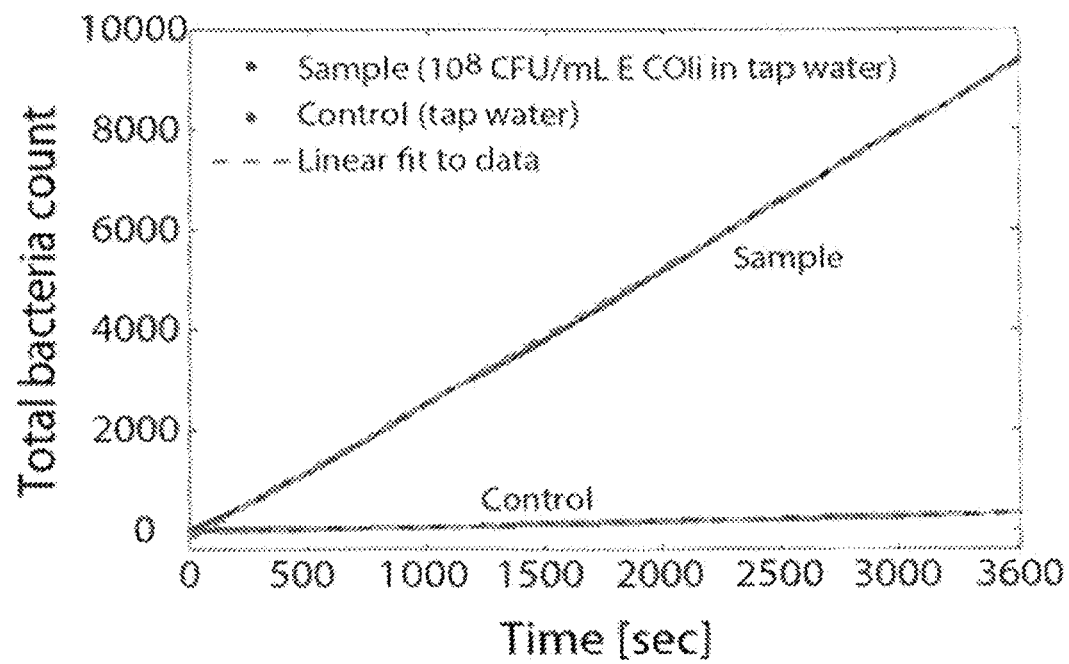
Figure 4B:
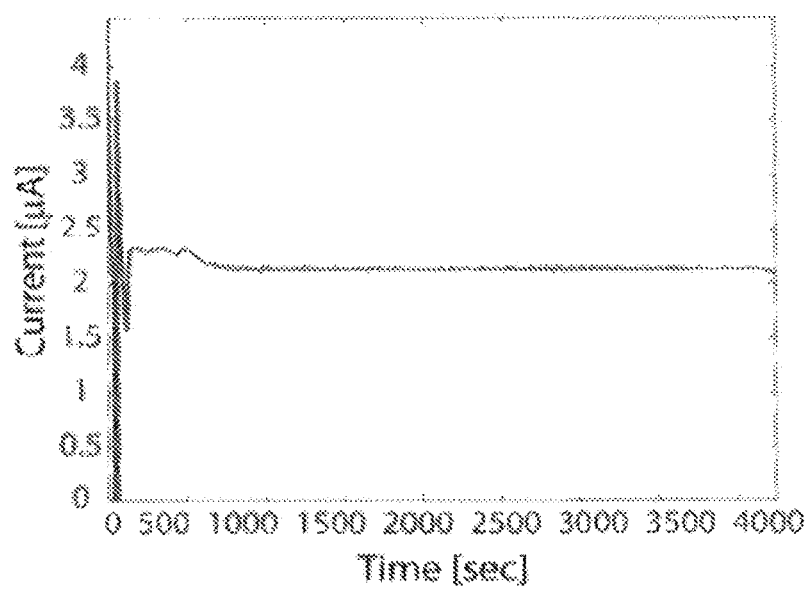

Using the same cross-section geometry, better limits of detection could be obtained with longer monitoring times. FIG. 4A presents bacteria count versus time and demonstrates continuous operation of the assay for over an hour. At a concentration of $10^8$ cfu/mL, we obtain approximately 9000 detections per hour (or 150 per minute). Importantly, the number of detected bacteria grows at a constant rate, substantiating and validating the assay stability and possible use as a continuous water monitoring platform. To further support the claim of the assay stability, a trace of the monitored current during the whole procedure is shown in FIG. 4B. Furthermore, no bacteria aggregation or channel clogging was observed during this 1 h time frame. As measured by Harden and Harris (Bacteriol. 1953, 65, 198) many other bacterial species are also negatively charged over a wide range of pH values, enabling their detection using the present assay. FIG. 4C presents the applicability of the assay to other (Gram-negative and Gram-positive) bacteria species.

The signal was acquired at 5 Hz frame rate for 2 min. The height of each bar represents the average of at least 5 realizations, with the range of the bars representing 95% confidence of the mean. Constant voltage of 400 V was applied on the channel, resulting in a current of approximately 2 µA.

Experimental measurements of bacteria counts vs time, demonstrating continuous bacterial detection during a 1 h period. The obtained signal exhibits stable behavior and increases linearly with time, suggesting no significant deterioration of the finite AMPs sample focused at the interface. The control sample contained only tap water and shows only a moderate increase, after long times, likely due to autofluorescence of contaminants or precipataion of AMPs. The signal was acquired at a 1 Hz frame rate for 1 h. Constant voltage of 400 V was applied on the channel.

Thus the present experiment enabled:
1. The design and use of positively charged labeled AMPs as universal probes for labeling and detecting bacteria.
2. The design of an ITP system (with an adequate chemistry) under which the AMPs are focused.
3. The formation of a high concentration AMPs zone that serves as a "virtual reaction chamber" for accelerated rapid binding of AMPs to bacteria outer membrane, thus labeling the bacteria.
4. Ability to continuously label, separate and detect bacteria in free solution, in one step.
5. Ability to quantify the initial bacteria concentration in sample, using the same method.

Example 2

Labeling Efficiency

Figure 7B:
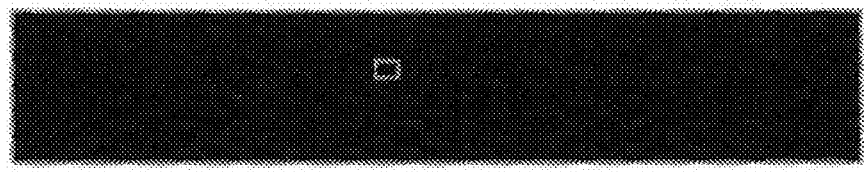

The sensitivity of the assay is directly affected by the flow rate, as well as the labeling efficiency of bacteria as it passes through the AMPs confined at the LE-TE interface. To characterize the latter, the assay was performed on tap water samples spiked with bacteria which were prelabeled with SYTO9. After stabilizing the assay, the counterflow and voltage were simultaneously stopped, such that all bacteria remain stationary. The channel was imaged at 10 stations downstream of the ITP interface zone. At each station, images were taken using two filters: 480/535 for detecting the bacteria prelabeled with SYTO9 and 545/605 for detecting the bacteria which were labeled on-chip by AMPs. SYTO9 emits at a wavelength of 500 nm, which is sufficiently shifted from the 579 nm emission of the TAMRA labeled AMPs, and thus, it is possible to measure the number of bacteria which were successfully labeled and compare it with the total number of bacteria that passed through the labeling zone. It should be clarified that the use of SYTO9 dye was not to monitor the viability of the bacteria but only to be able to count the total number of bacteria in frame. The labeling efficiency was defined as the ratio between the number of detected AMPs labeled bacteria and the total bacteria present in all the frames. To obtain additional statistics, the process was repeated several times by reapplying the current and counterflow to fill the channel with a new set of labeled bacteria. Imaging after stopping the flow enables one to perform this colocalization test of the signal, which is not possible during the standard assay operation. FIG. 7 illustrates this detection process.

The influence of both the applied current (affecting the electromigration speed of the bacteria) and the initial AMPs concentration (affecting the peak concentration at the ITP interface) was examined on the binding reaction of AMPs to the bacteria membrane. FIG. 5A presents the labeling efficiency as a function of the applied current to the channel. The average labeling efficiency varies between 65% and 85% for all the current values. The two sample t test method was used to determine whether the difference between any two measured mean values is significant. Using a p-value of p=0.05, the calculated t-values were significantly lower than the threshold required statistical significance (for example, the calculated t-value for the difference between the labeling efficiencies at 8 and 10 µA is 1.65, whereas the threshold based on the number of repeats is 2.78). Hence, to conclude, there is no significant advantage in the labeling efficiency of one current over another. This is despite the fact that higher current results in higher electromigration velocity and, consequently, shorter reaction time. This indicates that, at these electric current values, the labeling process is reaction limited and the advection time of the bacteria through the labeling zone is significantly higher than the time required for binding. It is hypothesize that at sufficiently high currents there would be a decrease in labeling efficiency as the advection time decreases. However, the highest current presented corresponds to the maximum voltage (2200 V) possible in the experimental setup disclosed herein, and this decrease could not be experimentally observed. Within the range of currents tested, the highest current is thus optimal, as it provides the highest flow rate, without reducing efficiency. FIG. 5B presents experimental results of labeling efficiency as a function of the AMPs concentration in the well, for a fixed current of 3 µA. Consistent with theory, labeling efficiency increases with AMPs concentration. It can concluded that the optimal concentration is 0.1 µM, as beyond this value significant precipitation of AMPs was observed, with no significant gain in signal (applying a t test analysis, the calculated t-value between the labeling efficiency at 0.1 and 1 µM is 1.12, whereas the critical t-value for 95% confidence is 2.31), suggesting no significant difference in labeling efficiency.

The invention claimed is:

1. A system comprising:
   (A) a protein having a domain that binds a bacterial membranal component;
   (B) a first flow channel configured to provide flow of a liquid sample to an isotachophoresis (ITP) apparatus, said liquid sample comprising or suspected of comprising a bacterial cell, a bacterial cell membrane or a fraction of a bacterial cell membrane; and
   (C) wherein said ITP apparatus comprises
      (a) a first zone and a second zone, said first zone is configured to contain a solution of high effective mobility leading electrolyte (LE) ion, and said second zone is configured to contain a solution of low effective mobility trailing electrolyte (TE) ion, said first zone and said second zone are configured to be operably connected to at least one anode and at least one cathode; and
      (b) at least one second flow channel elongated between said first zone and second zone;
   (D) a flow regulator, said flow regulator is configured to generate a flow countering an electromigration of said protein in the first flow channel so as to maintain said protein in a pre-determined zone.

2. The system of claim 1, wherein said membranal component is a protein.

3. The system of claim 1, wherein said liquid sample is continuously injected into said first flow channel.

4. The system of claim 1, wherein said membranal component is a net charge of phospholipid head groups or charge density of phospholipid head groups.

5. The system of claim 1, wherein said protein is labeled.

6. The system of claim 5, wherein said protein is labeled by at least one label selected from the group consisting of: fluorescently labeled, chemiluminescently labeled, radioactively labeled, and colorimetrically labeled.

7. The system of claim 1, wherein said protein is an anti-microbial peptide (AMP).

8. The system of claim 1, wherein said protein is an antibody or an antibody fragment.

9. The system of claim 1, comprising an anionic or cationic ITP focusing stationary zone characterized by high concentration of said protein.

10. The system of claim 1, wherein said LE comprises sodium hydroxide and/or wherein said TE comprises Pyridine.

11. The system of claim 1, further comprising a collector configured for collecting labeled cells from said second zone.

12. The system of claim 1, further comprising a detector selected from the group consisting of: a photodetector, a photomultiplier tube (PMT), a conductivity detector, a radioactive detector, a camera and any combination thereof.

13. The system of claim 1, wherein said bacterial cell is an intact bacterial cell.

14. A method for detecting a bacterial cell of interest, the method comprising the steps of:
   a) providing a labeled protein having a domain that binds a membranal component in said bacterial cell of interest, wherein said labeled protein is focused by ITP to an ITP zone in a liquid flow channel;
   b) applying a counter flow so as to maintain said labeled protein in a stationary zone;
   c) providing a sample to said flow channel, said sample comprising or suspected of comprising the bacterial cell of interest, a bacterial cell membrane or a fraction of a bacterial cell membrane thereof; and
   d) detecting said bacterial cell of interest bound to said labeled protein.

15. The method of claim 14, wherein said detecting includes labeling, separating, enriching, isolating, or any combination thereof.

16. The method of claim 14, wherein said detecting is achieved by using a photodetector, a photomultiplier tube (PMT), a conductivity detector, a radioactive detector, a camera or any combination thereof.

17. The method of claim 14, wherein said labeled is: chemiluminescently labeled, radioactively labeled, or colorimetrically labeled.

18. The method of claim 14, wherein said labeled protein is an anti-microbial peptide (AMP).

19. The method of claim 14, wherein said labeled protein is an antibody.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence

```
<220> FEATURE:
<223> OTHER INFORMATION: synthetic

<400> SEQUENCE: 1

Ile Leu Pro Trp Lys Trp Pro Trp Trp Pro Trp Arg Arg
1               5                   10
```